United States Patent [19]

Leibinsohn

[11] 4,373,524

[45] Feb. 15, 1983

[54] LIQUID FLOW CONTROL DEVICES PARTICULARLY USEFUL IN INFUSION ADMINISTRATION SETS

[76] Inventor: Saul Leibinsohn, 11 Oley Hagardom St., Rishon Le Zion, Israel

[21] Appl. No.: 148,487

[22] Filed: May 9, 1980

[30] Foreign Application Priority Data

May 14, 1979 [IL] Israel ........................................ 57279

[51] Int. Cl.³ ............................................... A61M 5/00
[52] U.S. Cl. .................................... 128/214 R; 251/4; 251/117
[58] Field of Search ............................ 251/342, 4, 117; 128/214 R, 214 F, 214 G

[56] References Cited

U.S. PATENT DOCUMENTS

| | | | |
|---|---|---|---|
| 3,675,891 | 7/1972 | Reynolds et al. ................ | 128/214 R |
| 4,106,675 | 8/1978 | Taylor ............................. | 251/342 X |
| 4,267,835 | 5/1981 | Barger et al. ..................... | 251/342 |

Primary Examiner—George J. Marlo
Attorney, Agent, or Firm—Benjamin J. Barish

[57] ABSTRACT

Liquid flow control devices are described particularly useful for attachment to an infusion administration set including an infusion liquid container connected by a line to an infusion needle, comprising: a conical socket member at one end of the device for connecting same to the infusion container side of the line; a conical pin member at the opposite end of the device for connecting same to the infusion needle side of the line; and fixed-rate liquid metering components including a stem formed with a metering groove and an overlying sleeve, the metering components being located between and communicating with the socket and pin members for metering the liquid flow therebetween according to a preselected fixed rate. The overlying sleeve is resilient and includes a pair of spaced apart protuberances which provide a finger gripping portion and enable the resilient sleeve to be deformed for providing an enlarged flushing passageway for the liquid.

26 Claims, 18 Drawing Figures

LIQUID FLOW CONTROL DEVICES PARTICULARLY USEFUL IN INFUSION ADMINISTRATION SETS

BACKGROUND OF THE INVENTION

The present invention relates to liquid flow control devices, and particularly to such devices useful in infusion administration sets.

Infusion administration sets include an infusion liquid container connected by a line to an infusion needle. The rate of flow of the liquid from the container to the needle is commonly controlled by a roller clamp provided in the line. However, such roller clamps are not accurate to provide a precise preselected rate of flow of the liquid to the needle; moreover, their setting is not particularly stable and changes during the period of use. Accordingly, an infusion procedure utilizing such roller clamps frequently requires monitoring by the nurse on duty, which may be burdensome on the hospital staff particularly in view of the chronic shortage of nurses faced by most hospitals.

BRIEF SUMMARY OF THE INVENTION

An object of the present invention is to provide a liquid flow control device particularly useful in infusion administration sets to avoid the above drawbacks in the existing sets.

According to a broad aspect of the present invention, there is provided a liquid flow control device particularly useful for attachment to an infusion administration set including an infusion liquid container connected by a line to an infusion needle, comprising: a conical socket member at one end of said device for connecting same to the infusion container side of the line; a conical pin member at the opposite end of said device for connecting same to the infusion needle side of the line; and fixed-rate liquid metering means between and communicating with said socket and pin members for metering the liquid flow therebetween according to a preselected fixed rate. The fixed-rate liquid metering means includes a stem integrally formed with one of the conical members, a sleeve overlying the stem, and a metering groove formed between the outer face of the stem and the inner face of the overlying sleeve, which groove meters the liquid flow according to the preselected fixed rate.

A number of embodiments of the invention are described below for purposes of example. In most of the described embodiments, the overlying sleeve is a resilient tube, the socket member and stem being received in one end of the resilient tube with the socket member facing outwardly and its stem facing inwardly, the pin member being received in the opposite end of the resilient tube in axially spaced relationship from the stem of the socket member.

Liquid flow control devices constructed in accordance with the above features provide a number of important advantages particularly when used in infusion administration sets. Thus, they permit the infusion liquid to be fed to the infusion needle at a preselected precise rate by merely attaching the appropriate liquid flow control device to the line. The administration set would preferably be provided with a plurality of such liquid flow control devices, e.g., colour-coded according to different rates, which the attendent may select for each particular case and attach to the line between the infusion liquid container and the infusion needle. In addition, the overlying resilient tube, being deformable, provides an enlarged flushing passageway for the liquid, should the flushing of the passageway be required as it is on occasions. Special constructions are described below to facilitate the deformation of the tube to produce the flushing action. Further, the axial spacing between the stem of the socket member and the pin member permits injection of a substance by penetrating the resilient tube with a hyperdermic needle, which is also required on occasions.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
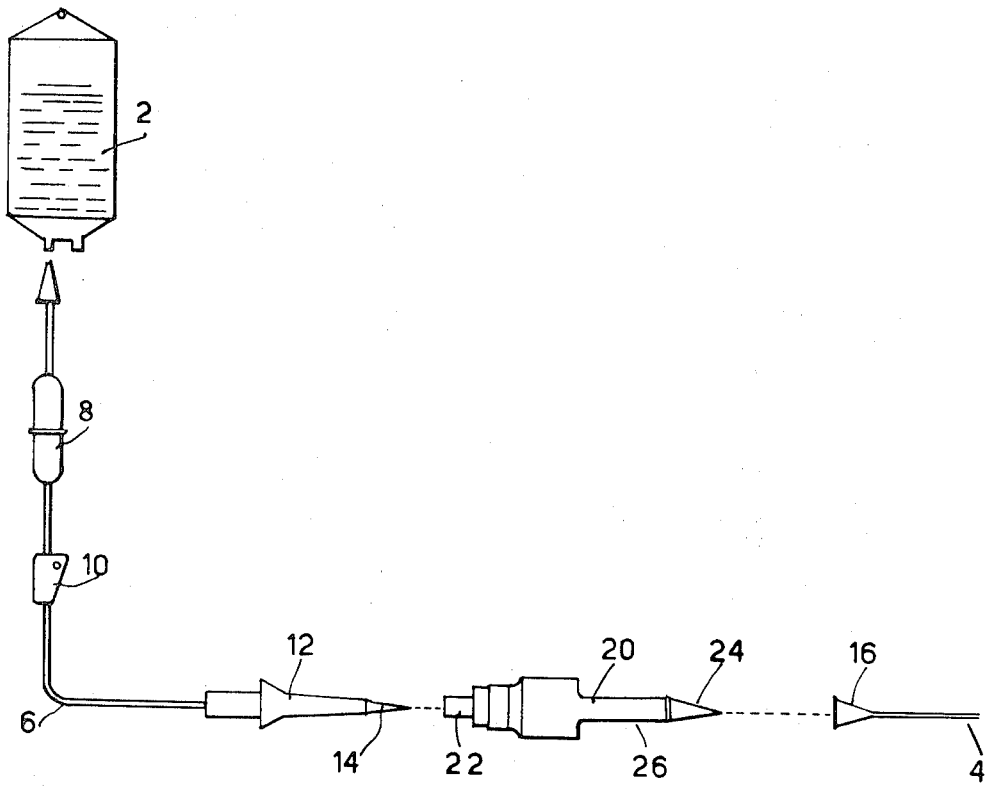
FIG. 1 illustrates an infusion administration set including a liquid flow control device constructed in accordance with the invention.

With reference first to FIG. 1, there is illustrated an infusion administration set including an infusion container 2 containing the infusion liquid, and an infusion needle 4 connected to container 2 by a line 6, usually of a rubber tube. Line 6 further includes a drip chamber 8, a roller clamp 10 for controlling the rate of flow of the infusion liquid, and an injection piece 12 which may be used by the attendent to inject a substance into the incusion liquid by penetrating the injection piece with a hyperdermic needle. The injection piece 12 commonly terminates in a conical pin 14 which is adapted to be received in a conical socket 16 carried by the needle 4 or a line connected to it.

In accordance with the present invention, a liquid flow control device, generally designated 20, is included in the line between the infusion container 2 and the infusion needle 4 for metering the liquid flow according to a preselected fixed rate. It may be simply connected into the line between the injection piece 12 and the infusion needle 4 with the roller clamp 10 in its fully open position, or it may be used in an infusion administration set in lieu of the roller clamp 10, and/or the injection piece 12, as will be more readily apparent from the description below.

Figure 2:
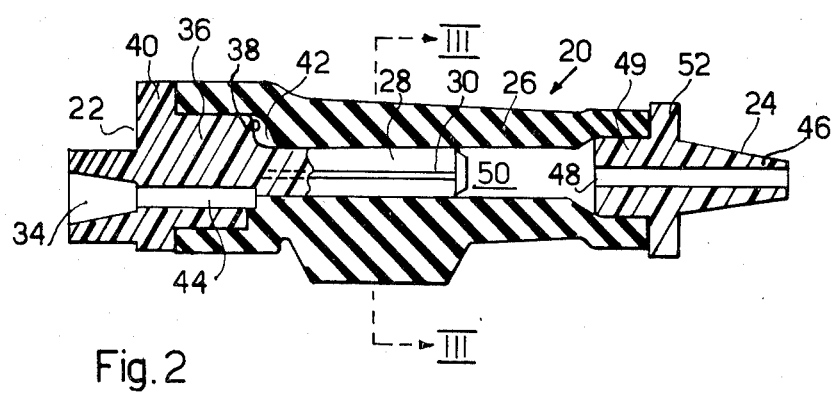
FIG. 2 is an enlarged longitudinal sectional view of the liquid flow control device in the set of FIG. 1.
Figure 3:
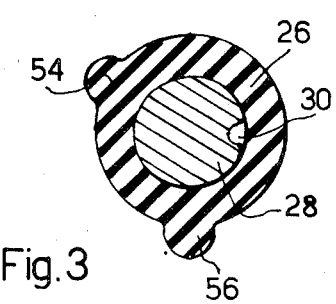
FIG. 3 is a transverse sectional view along lines III—III of FIG. 2.

With reference to FIGS. 2 and 3, the liquid flow control device 20 comprises three main members, namely a conical socket member 22 disposed at one end, a conical pin member 24 disposed at the opposite end, and a resilient tube 26 connecting the two members together. The metering of the liquid causing it to flow according to a fixed rate is effected by a stem 28 integrally formed with the socket member 22, which stem is provided with a metering groove 30 cooperable with the inner face of the resilient tube 26 to define a precise metering passageway for the liquid flowing through the device.

More particularly, the socket member 22, preferably of a molded plastics material, is formed on one face with a conical socket cavity 34 adapted to receive pin 14 of the injection piece 12. Socket member 22 is further formed with a radially-thickened portion 36 defining a shoulder 38 between it and the stem 28 projecting from the opposite face of the socket member 22. The end of the resilient tube 26 is received on the thickened portion 36 and abuts against an end flange 40. When so received, the resilient tube defines a small annular space 42 between its inner face and the bottom corner of shoulder 38, which annular space 42 communicates with the metering groove 30 formed on the outer face of stem 28.

As shown in FIG. 2, the conical socket cavity 34 is formed eccentrically with respect to the axis of stem 28, and is further formed with an axially-extending bore 44 providing communication between the socket 34 and the annular space 42, and thereby with the metering groove 30.

The pin connector member 24, similarly of molded plastics material, is formed with a conical pin 46 on its outer end for reception in the conical pocket 16 of the needle 4, and with an axial bore 48 for feeding the liquid therethrough. Its inner end 49 is spaced from the inner end of stem 30 to define a chamber 50, and is of cylindrical configuration for receiving the end of resilient tube 26, which end limits against a flange 52 on member 24.

Figure 3A:
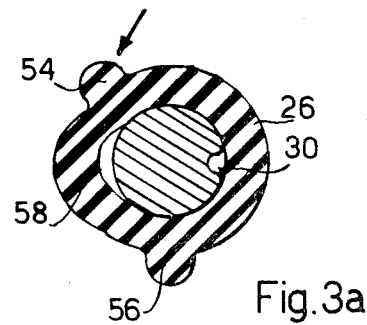
FIG. 3a is a view similar to that of FIG. 3 but illustrating how the overlying resilient tube may be deformed to provide an enlarged flushing passageway for the liquid.

Resilient tube 26 may be made of rubber, for example. The portion of tube 26 overlying stem 28 is formed with a pair of protuberances 54, 56 (FIGS. 3, 3a) angularly spaced from each other less than 180°, for example about 135°. These protuberances 54, 56 serve as finger-gripping elements on the resilient tube enabling the attendant, by pressing the protuberances towards each other as shown in FIG. 3a, to deform the tube 26 and thereby to provide an enlarged flushing passageway 58, as shown in FIG. 3a, which flushing passageway by-passes the metering groove 30 in stem 28, permitting a large quantity of the liquid to be flushed through the needle 4.

It will be seen that the device illustrated in FIG. 2 may be quickly attached to the infusion administration set by merely inserting conical pin 14 of the injection piece 12 into the conical socket cavity 34 of the metering device, and conical pin 46 of the latter device into conical socket 16 of the needle 4. When so inserted, the device will provide a precise metering of the liquid flowing from the infusion container 2 to the needle 4. As such, it could replace the roller clamp 10 commonly included in such infusion administration sets.

The liquid flow control device 20 could also replace the injection piece 12, since chamber 50 between stem 28 and the conical pin member 24 permits the injection of a substance into the liquid flowing through the device by penetrating the resilient tube 26 with a hyperdermic needle at the portion of the tube enclosing this chamber.

Figure 4:
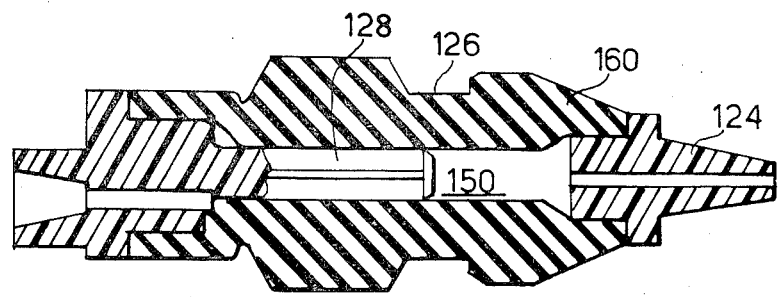
FIG. 4 is a longitudinal sectional view illustrating another form of liquid flow control device constructed in accordance with the invention.

FIG. 4 illustrates a modification wherein a thickened annular rib 160 is formed on the outer surface of the resilient tube 126, the hyperdermic needle being insertable through rib 160 to inject the substance into the space 150 between the metering stem 128 and the conical pin member 124.

Figure 5:
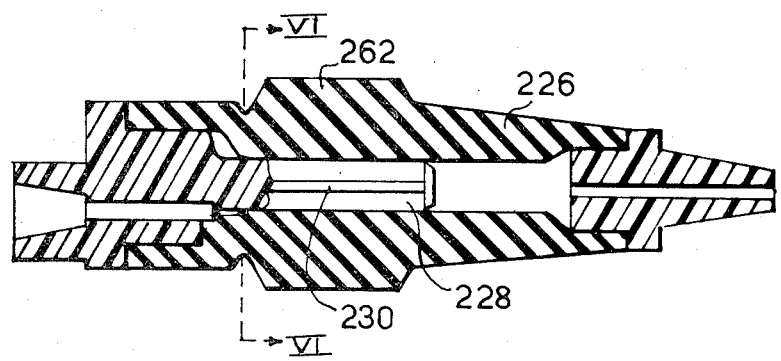
FIG. 5 is a longitudinal sectional view illustrating another form of liquid flow control device constructed in accordance with the invention.
Figure 6:
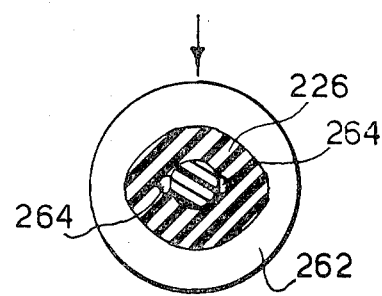
FIG. 6 is a transverse sectional view along lines VI—VI of FIG. 5.

FIGS. 5 and 6 illustrate a further modification in the device for producing the flushing action by deforming the outer resilient tube, therein generally designated 226. In the modification of FIGS. 5 and 6, the resilient tube 226 is provided with a thickened rib 262 at the portion thereof in alignment with the metering stem 228, such that by merely squeezing the thickened rib 262, the portion of the tube overlying the metering stem is deformed into an elliptical shape so that its inner face forms flushing passageways 264 at the opposite side of the metering stem 228, by-passing its metering groove 230 to flush the liquid through the device.

Figure 7:
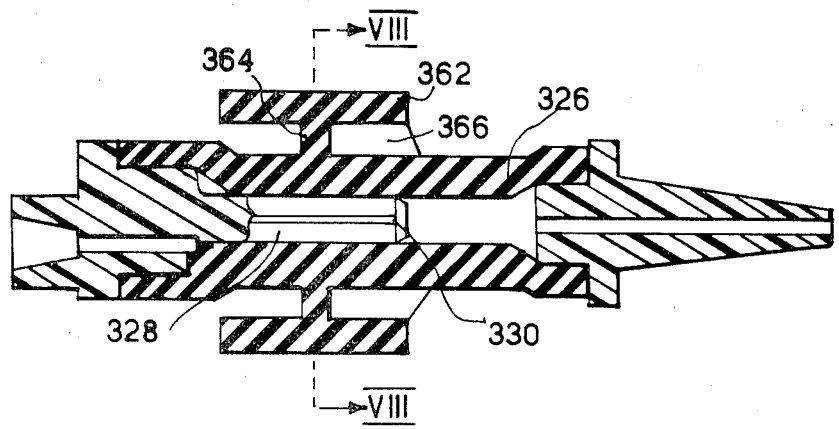
FIG. 7 is a longitudinal sectional view of a further form of liquid flow control device constructed in accordance with the invention.
Figure 8:
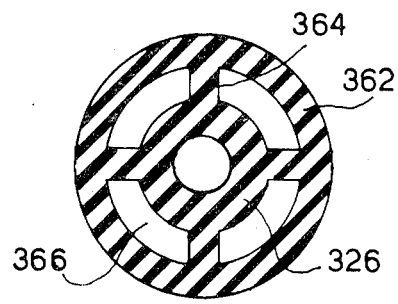
FIG. 8 is a transverse sectional view along lines VIII—VIII of FIG. 7.

Another arrangement is illustrated in FIGS. 7 and 8 for flushing the liquid through the device. In this arrangement, the outer surface of the resilient tube 326 carries an annular ring 362 integrally formed and joined to the resilient tube by means of a central radially-extending rib 364 and a plurality of axially-extending ribs 366. Thus, when ring 362 is squeezed, the portion of the resilient tube 326 overlying stem 328 is deformed to provide an enlarged passageway for causing the liquid to by-pass metering groove 330.

Figure 9:
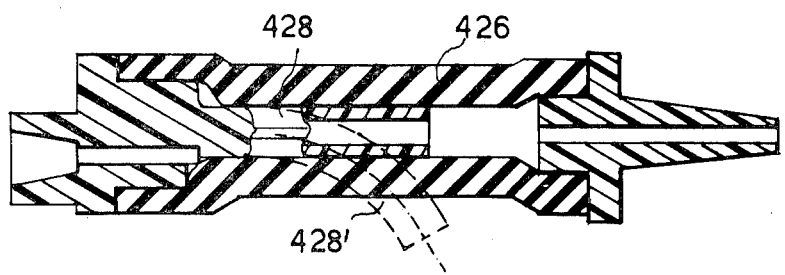
FIGS. 9 and 10 are longitudinal sectional views illustrating two further forms of liquid flow control devices constructed in accordance with the invention.

FIG. 9 illustrates a still further flushing arrangement, wherein the metering stem 428 is made of stiff elastic material enabling it to be bent, as shown by the broken lines 428'. This bending of the stem causes it to form enlarged passageways between its outer surface and the inner surface of the resilient tube 426 permitting the flushing of the device.

Figure 10:
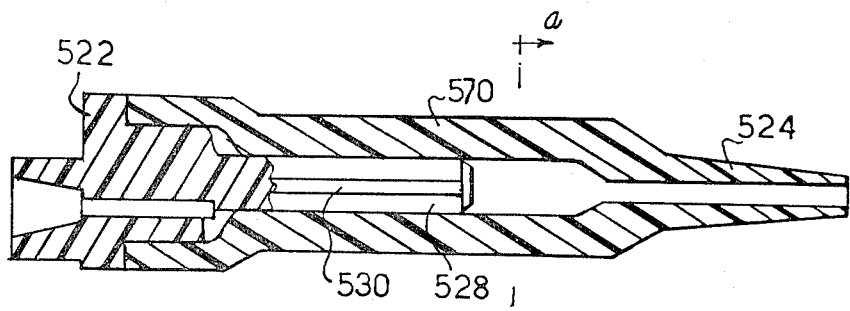

FIG. 10 illustrates a still further embodiment made of but two parts and therefore less costly to produce. In this embodiment, the resilient tube is omitted, and instead, the inner end of the conical pin member 524 is extended to serve as a sleeve 570 received on the conical socket member 522 and its metering stem 528. Preferably, pin member 524, including its extension sleeve 570, is made of flexible material to permit the sleeve 570 to be applied to the socket member 522, and the conical pin end 524 of the member is thickened to impart stiffness to that end.

Figure 10A:
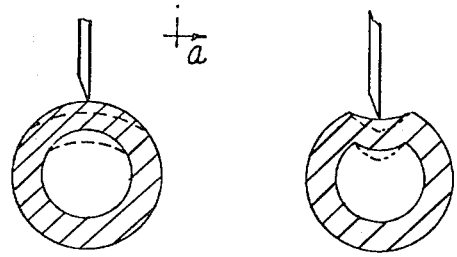
FIG. 10a is a sectional view along lines a—a of FIG. 10.
Figure 10B:
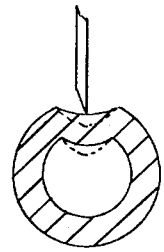
FIG. 10b is a view corresponding to FIG. 10a but illustrating a modification.

As shown in FIG. 10a, if sleeve 570 is of cylindrical section, piercing it with a hyperdermic needle tends to deform it inwardly flattening the sleeve at that point, so that, when the needle is removed and the sleeve restored to its original shape, the hole formed by the needle enlarges, thus tending to leak. This can be avoided by making the tube of a convex outer shape at the point of entry of the needle, as shown in FIG. 10b, so that the deformation of the sleeve will decrease the radius of curvature, and thereby decrease the size of the hole and the tendency to leak, when the needle is removed.

Figure 11:
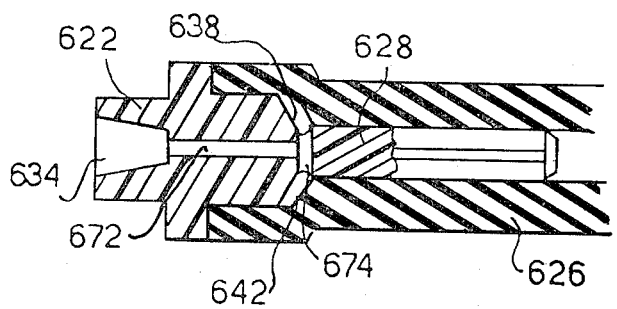
FIGS. 11 and 12 illustrate modifications in the structure of the conical socket member which may be used in any of the previously-illustrated liquid flow control devices.

FIG. 11 illustrates a modified construction of the socket member, therein designated 622. In this modification, the conical socket cavity 634 is formed concentrically to its metering stem 628 and communicates with the annular space 642 formed between its shoulder 638 and the inner face of the resilient tube 626 by means of an axially-extending bore 672 from cavity 634 joined to a radially-extending bore 674 leading to the annular space 642.

Figure 12:
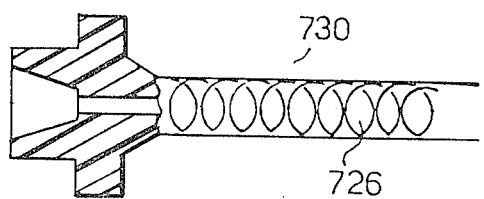

FIG. 12 illustrates a modified stem construction wherein the stem 726 is formed with a helical metering groove 730, rather than an axially-extending one. Such an arrangement increases the length of the groove and thereby permits more precise metering of the liquid in a more compact space.

It will be appreciated that the modifications of FIGS. 11 and 12 may be included in any of the herein-described embodiments.

Figure 13:
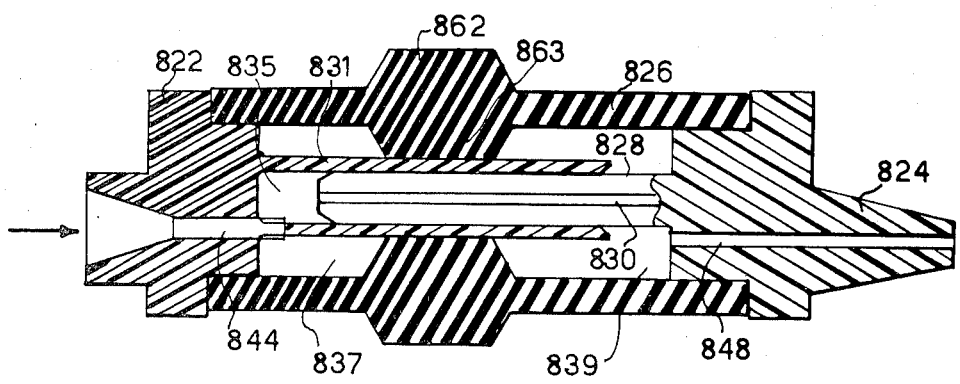
FIGS. 13 and 14 are longitudinal sectional views of two further forms of liquid flow control device constructed in accordance with the invention, FIG. 14a being a sectional view along lines a—a of FIG. 14.

FIG. 13 illustrates a further construction for producing the flushing action. The construction of FIG. 13 also includes three main members, namely a conical socket member 822, a conical pin member 824, and a resilient tube 826 connecting them together. Here, however, the stem 828 including the metering groove 830 is formed integrally with the conical pin member 824, and is adapted to be snugly received within a sleeve 831 formed integrally with the socket member 822. Bore 844 through socket member 822 also penetrates partly through sleeve 831, so that this bore provides communication to the space 835 interiorly of sleeve 831, as well as to an annular chamber 837 formed externally of the sleeve between it and the resilient tube 826.

Resilient tube 826 is formed with an annular rib 862 on its outer surface, as well as with an annular rib 863 on its inner surface engaging sleeve 831 so as normally to seal-off the annular chamber 837. Accordingly, the liquid inletted through bore 844, will fill chamber 837, but will normally pass only through the metering groove 830 to another annular chamber 839 at the opposite side of the inner rib 863. From chamber 839, this liquid passes out through an axial bore 848 in the pin member 824.

Whenever it is desired to flush the device, thickened rib 862 is squeezed, thereby deforming the resilient tube 826 to provide an enlarged flushing passageway between its internal rib 863 and the internal face of sleeve 831. Accordingly, the liquid within the annular chamber 837 is permitted to be flushed out through this passageway and, via chamber 839, through bore 848 in the pin member 824.

In the device of FIG. 13, the socket member 822, and its sleeve 831, are preferably of rigid material, and similarly the pin member 824 and its stem 828 are also preferably of rigid material. Accordingly, the metering passageway defined by groove 830 in stem 828, and the inner surface of sleeve 831, does not yield under pressure, thereby providing a precise metering of the fluid through the device. When it is desired to flush the device, rib 862 is squeezed, causing the flushing liquid to by-pass the metering groove 830, as described above.

Figures 14, 14A:
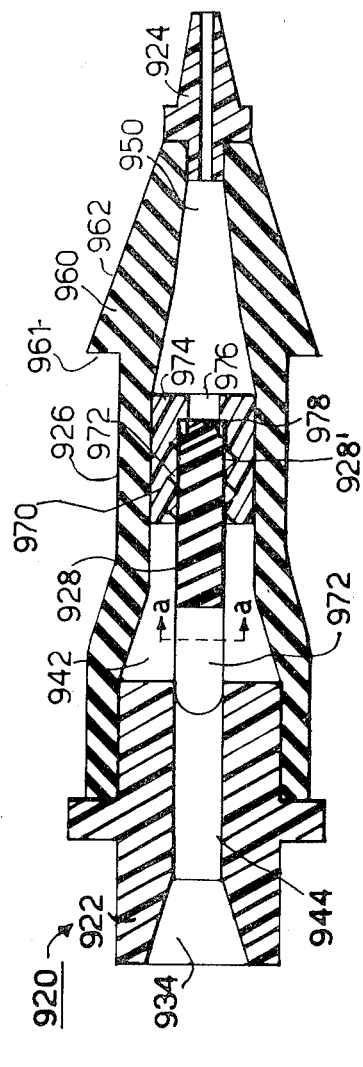

The liquid flow control device illustrated in FIGS. 14 and 14a is generally designated 920 and comprises a conical socket member 922, a conical pin member 294, and a resilient tube 926 connecting the two members together. The conical socket member 922 is formed with a stem 928, but in this case the metering of the liquid, causing it to flow according to a fixed rate, is effected by a groove formed between the outer face of stem 928 and a newly-added overlying sleeve 970.

More particularly, the metering groove, designated 972 in FIG. 14 is formed on the inner face of the sleeve 970 and is of helical configuration. Sleeve 970 is formed with an end wall 974 having an opening 976 at its center of smaller diameter than the outer diameter of stem 928, to define a shoulder engaging the end of the stem, thereby limiting the position of this sleeve on the stem. Further, the end of the stem is pinched, as shown at 928', to define, with sleeve 970, an annular space 978 providing communication between the end of groove 972 and the opening 976 in the sleeve end wall 974.

It will be seen from FIG. 14 that the sleeve 970 is of shorter length than the stem 928 and occupies the end of the stem facing the conical pin member 924, thereby defining, with the resilient tube 926, an annular space 942 around the stem at the end thereof facing the conical socket member 922. The conical socket cavity 934 in member 922 communicates with this annular space 942 via an axial bore 944 and a radial bore 972.

As can be seen from FIG. 14, the conical pin connector member 924 is spaced in the axial direction from the end of stem 928 and its sleeve 970 to define a chamber 950. The outer resilient tube 926 is provided at this location with a thickened annular rib 960 defined by a radial wall 960 and a tapered wall 962. A hypodermic needle may be inserted through the radial wall 961 of rib 960 to inject a substance into the chamber 950 to be added to the liquid flowing through this chamber and out through line conical pin member 924.

The device illustrated in the drawings may be subjected to a flushing action by squeezing the resilient tube 926 overlying the sleeve 970, whereupon the resilient tube is deformed to provide passageways bypassing the metering groove 972 for flushing the liquid through the device.

In all other respects, the construction and operation of the device illustrated in FIGS. 14 and 14a are the same as described in the other embodiments.

While the invention has been described with respect to a number of preferred embodiments set forth for purposes of example, it will be appreciated that many variations, modifications and applications of the invention may be made.

What is claimed is:

1. A liquid flow control device particularly useful for attachment to an infusion administration set including an infusion liquid container connected by a line to an infusion needle, comprising: a conical socket member at one end of said device for connecting same to the infusion container side of the line; a conical pin member at the opposite end of said device for connecting same to the infusion needle side of the line; and fixed-rate metering means between and communicating with said socket and pin members for metering the liquid flow therebetween according to a preselected fixed rate; said fixed-rate liquid metering means including a stem integrally formed with one of said conical members, a sleeve overlying said stem, and a metering groove formed between the outer face of the stem and the inner face of the overlying sleeve which groove meters the liquid flow according to the preselected fixed rate.

2. A device according to claim 1, wherein said stem is integrally formed with said conical socket member.

3. A device according to claim 2, wherein said overlying sleeve is a resilient tube, said socket member and stem being received in one end of the resilient tube with the socket member facing outwardly and its stem facing inwardly, said pin member being received in the opposite end of the resilient tube in axially spaced relationship from the stem of said socket member.

4. A device according to claim 3, wherein the portion of the resilient tube overlying said stem is deformable to provide an enlarged flushing passageway for the liquid.

5. A device according to claim 4, wherein said resilient tube includes a finger gripping portion for deforming the tube overlying the stem to provide said enlarged flushing passageway for the liquid.

6. A device according to claim 5, wherein said finger-gripping portion comprises a pair of protuberances formed on the outer surface of the resilient tube angularly spaced from each other a distance of less than 180°.

7. A device according to claim 3, wherein said overlying resilient tube includes a thickened rib overlying the space between said stem and pin member to permit injection of a substance into said space by penetrating said thickened rib with a hyperdermic needle.

8. A device according to claim 3, wherein said resilient tube includes a convex portion for penetration with a hyperdermic needle.

9. A device according to claim 5, wherein said finger-gripping portion comprises a thickened annular rib formed on the outer surface of the resilient tube.

10. A device according to claim 5, wherein said finger-gripping portion comprises an outer annular ring integrally formed with and joined to the resilient tube by a plurality of axially-extending ribs.

11. A device according to claim 1, wherein said sleeve overlying said stem is integrally formed with said conical pin member.

12. A device according to claim 1, wherein said conical socket member is a unitary member of plastics material having a conical socket cavity formed in one face and the stem projecting from the opposite face.

13. A device according to claim 12, wherein said conical socket member is formed with a radially-thickened portion defining a shoulder with the inner end of said stem, said radially-thickened portion receiving one end of said resilient tube such that the tube defines an annular space between its inner face and the bottom corner of said shoulder which annular space communicates with the inner end of said metering groove formed in said stem, said conical socket member further including a passageway providing communication between said conical socket cavity and said space.

14. A device according to claim 13, wherein said conical socket cavity is formed eccentrically to said stem and communicates with said annular space by an axially-extending bore.

15. A device according to claim 13, wherein said conical socket cavity is formed concentrically to said stem and communicates with said annular space by axially-extending and radially-extending bores.

16. A device according to claim 1, wherein said stem is integrally formed with said pin member.

17. The device according to claim 16, wherein both said sleeve and stem are rigid material, the device further including a resilient tube enclosing said sleeve and formed with an internal annular rib in contact with the outer face of the sleeve, said resilient tube being deformable by squeezing same to provide a flushing passageway for the liquid between said rib and the outer face of the sleeve.

18. A device according to claim 1, wherein said metering groove is formed on the outer surface of the stem parallel to its longitudinal axis.

19. A device according to claim 1, wherein said metering groove is formed on the outer surface of the stem helically thereof.

20. A liquid flow control device according to claim 1, wherein the inner face of the sleeve is formed with said metering groove.

21. A device according to claim 20, wherein said metering groove is of helical configuration.

22. A device according to claim 20 wherein said sleeve is formed with an end wall at the end thereof opposite to said conical socket member, said end wall having an opening of smaller diameter than said stem to define a shoulder engaging the end of the stem to limit the position of the sleeve on the stem.

23. A device according to claim 22, wherein said end of the stem is pinched to define, with said sleeve, a space providing communication between the end of said groove in the sleeve and the opening in the sleeve end wall.

24. A device according to claim 20, further including a resilient tube overlying said sleeve and interconnecting said conical socket member with said conical pin member.

25. A device according to claim 24, wherein said sleeve is of shorter length than said stem and is spaced from the end thereof facing the conical socket member thereby defining, with said resilient tube, an annular space around the stem at the end thereof facing said conical socket member, said latter end of the stem being formed with an axial bore joined to a radial bore from the inlet of the conical socket member.

26. An infusion administration set comprising an infusion container, an infusion needle, a line connecting said needle to said container and a fixed rate liquid flow control device according to claim 1 connected in said line.

* * * * *